United States Patent
Shong et al.

(10) Patent No.: US 9,605,198 B2
(45) Date of Patent: *Mar. 28, 2017

(54) MIXED CARBON LENGTH SYNTHESIS OF PRIMARY GUERBET ALCOHOLS

(71) Applicant: Chevron U.S.A. Inc., San Ramon, CA (US)

(72) Inventors: Robert Shong, Houston, TX (US); Varadarajan Dwarakanath, Houston, TX (US); Sophany Thach, Houston, TX (US); Gregory Winslow, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/673,425

(22) Filed: Mar. 30, 2015

(65) Prior Publication Data
US 2015/0203740 A1 Jul. 23, 2015

Related U.S. Application Data

(63) Continuation-in-part of application No. 13/835,030, filed on Mar. 15, 2013, now abandoned, and a
(Continued)

(51) Int. Cl.
*E21B 43/16* (2006.01)
*C09K 8/58* (2006.01)

(52) U.S. Cl.
CPC ............... *C09K 8/58* (2013.01); *E21B 43/16* (2013.01)

(58) Field of Classification Search
CPC .................. C09K 8/58; E21B 43/16
See application file for complete search history.

(56) References Cited

U.S. PATENT DOCUMENTS

| 2,757,139 A | 7/1956 | Matuszak |
| 3,437,141 A | 4/1969 | Brandner et al. |

(Continued)

FOREIGN PATENT DOCUMENTS

| DE | 3901318 | 7/1990 |
| EP | 0037542 A2 | 10/1981 |

(Continued)

OTHER PUBLICATIONS

Pandey, Amitabh, "Refinement of Chemical Selection for the Planned ASP Pilot in Mangala Field—Additional Phase Behaviour and Coreflood Studies", SPE 129064, SPE Oil and Gas India Conference and Exhibition held in Mumbai, India, Jan. 20-22, 2010, 9 pages.

(Continued)

*Primary Examiner* — Zakiya W Bates
*Assistant Examiner* — Crystal J Miller
(74) *Attorney, Agent, or Firm* — Karen R. DiDomenicis (57) ABSTRACT

In an embodiment of the disclosure, mixtures of different carbon length alcohols are used as the primary feedstock for Guerbet alcohols. Specifically, embodiments relate to a method of synthesizing mixed molecular weight additives from a mixture of primary alcohols comprising, receiving a mixture of primary alcohols comprising at least two different chain length primary alcohols and reacting the mixture of primary alcohols to produce a mixture of Guerbet alcohols. The mixture of Guerbet alcohols is then used to produce an additive composition comprising additives of different molecular weights.

12 Claims, 2 Drawing Sheets

Related U.S. Application Data continuation-in-part of application No. 13/833,045, filed on Mar. 15, 2013, and a continuation-in-part of application No. 13/233,406, filed on Sep. 15, 2011, now abandoned.

(56) References Cited

U.S. PATENT DOCUMENTS

| | | | |
|---|---|---|---|
| 3,769,022 A | 10/1973 | Ville et al. | |
| 3,844,350 A | 10/1974 | Knight et al. | |
| 4,004,638 A | 1/1977 | Burdyn et al. | |
| 4,518,810 A | 5/1985 | Matsuda | |
| 4,759,931 A | 7/1988 | van Paassen | |
| 4,830,769 A | 5/1989 | O'Lenick, Jr. et al. | |
| 5,100,573 A | 3/1992 | Balzer | |
| 5,180,584 A | 1/1993 | Sebag et al. | |
| 5,250,727 A | 10/1993 | Fried | |
| 5,290,838 A | 3/1994 | Hashimoto | |
| 5,387,374 A | 2/1995 | Westfechtel | |
| 5,391,822 A | 2/1995 | Fried | |
| 5,717,119 A | 2/1998 | O'Lenick, Jr. | |
| 6,060,443 A | 5/2000 | Cripe | |
| 6,136,894 A | 10/2000 | Stark et al. | |
| 6,234,183 B1* | 5/2001 | Chan | C09K 8/524 134/22.1 |
| 6,342,473 B1 | 1/2002 | Kott | |
| 6,439,308 B1 | 8/2002 | Wang | |
| 6,664,429 B1 | 12/2003 | Huebner et al. | |
| 6,692,539 B2 | 2/2004 | Desenne et al. | |
| 7,037,884 B2 | 5/2006 | Man | |
| 7,119,125 B1* | 10/2006 | O'Lenick, Jr. | B01F 17/0057 516/25 |
| 7,208,118 B2 | 4/2007 | Leinweber et al. | |
| 7,297,167 B2 | 11/2007 | Desenne et al. | |
| 7,985,718 B2 | 7/2011 | Steinbrenner | |
| 7,989,399 B2 | 8/2011 | Stoian | |
| 8,053,396 B2 | 11/2011 | Huff | |
| 8,211,837 B2* | 7/2012 | Weerasooriya | 507/253 |
| 8,235,120 B2 | 8/2012 | Quintero et al. | |
| 8,524,643 B2 | 9/2013 | Juergen | |
| 8,841,241 B2* | 9/2014 | Weerasooriya | C09K 8/584 166/902 |
| 8,946,490 B2* | 2/2015 | Mirk | C07C 29/149 568/885 |
| 9,109,152 B2* | 8/2015 | Weerasooriya | C09K 8/584 |
| 9,206,347 B2* | 12/2015 | Weerasooriya | C09K 8/584 |
| 9,296,942 B2* | 3/2016 | Weerasooriya | C09K 8/584 |
| 2003/0181770 A1 | 9/2003 | Both et al. | |
| 2003/0182734 A1 | 10/2003 | Desenne et al. | |
| 2008/0261835 A1 | 10/2008 | Berger et al. | |
| 2009/0151941 A1 | 6/2009 | Dwarakanath et al. | |
| 2009/0279281 A1 | 11/2009 | Chung | |
| 2011/0059872 A1* | 3/2011 | Weerasooriya | C09K 8/584 507/219 |
| 2011/0071057 A1* | 3/2011 | Weerasooriya | C07D 301/00 507/219 |
| 2011/0220366 A1 | 9/2011 | Bittner | |
| 2011/0259583 A1 | 10/2011 | Bittner | |
| 2011/0263467 A1 | 10/2011 | Bittner | |
| 2011/0281779 A1* | 11/2011 | Weerasooriya | C09K 8/584 507/254 |
| 2011/0290482 A1 | 12/2011 | Weerasooriya et al. | |
| 2012/0083631 A1* | 4/2012 | Mirk | C07C 29/149 568/885 |
| 2012/0097389 A1 | 4/2012 | Dwarakanath et al. | |
| 2013/0068457 A1 | 3/2013 | Thach | |
| 2013/0098612 A1 | 4/2013 | Bittner | |
| 2013/0102505 A1 | 4/2013 | Bittner | |
| 2013/0277276 A1* | 10/2013 | Weerasooriya | C09K 8/584 208/435 |
| 2014/0182851 A1* | 7/2014 | Weerasooriya | C09K 8/584 166/270.1 |
| 2016/0069168 A1* | 3/2016 | Weerasooriya | C09K 8/584 507/240 |

FOREIGN PATENT DOCUMENTS

| | | |
|---|---|---|
| EP | 0580263 | 10/1997 |
| FR | 2680682 | 9/1991 |
| GB | 1302880 | 1/1973 |
| GB | 2088863 | 6/1982 |
| GB | 2132664 | 7/1984 |
| JP | 04-149112 | 5/1992 |
| JP | 2000-351990 | 12/2000 |
| JP | 2002-241789 | 8/2002 |
| JP | 4864239 | 2/2012 |
| WO | 2008/079855 | 7/2008 |
| WO | 2010/090901 | 8/2010 |
| WO | 2011/037975 A2 | 3/2011 |
| WO | 2011/037975 A3 | 3/2011 |
| WO | 2011037975 | 3/2011 |
| WO | 2011037975 | 7/2011 |
| WO | 2011/130310 | 10/2011 |
| WO | 2011130310 | 10/2011 |
| WO | 2013/060622 | 5/2013 |
| WO | 2013/060623 | 5/2013 |
| WO | 2013/060670 | 5/2013 |
| WO | 2013/120757 | 8/2013 |
| WO | 2013/167438 | 11/2013 |

OTHER PUBLICATIONS

Pandey, et al., "Design of an ASP Pilot for the Mangala Field: Laboratory Evaluations and Simulation Studies" SPE 113131, 2008 Indian Oil and Gas Technical Conference and Exhibition in Mumbai, India Mar. 4-6, 2008. 9 pages.

Levitt, et al., "Identification and Evaluation of High-Performance EOR Surfactants" Apr. 2009 SPE Reservoir Evaluation & Engineering, pp. 243-253.

Falls, et al., "Field Test of Cosurfactant-Enhanced Alkaline Flooding", Aug. 1994, SPE Reservoir Engineering, pp. 217-223.

Zheng et al., Optimization of fatty alcohol biosynthesis pathway for selectively enhanced production of C12/14 and C16/18 fatty alcohols in engineered *Escherichia coli*, 2012 BioMed Central, Microbial Cell Factories, 11 pages.

O'Lenick, Jr., "A Review of Guerbet Chemistry", Journal of Surfactants and Detergents, Publisher Springer Berlin/Heidelberg, pp. 1-16, vol. 4, No. 3, Jul. 1, 2001.

Salazar, Jean-Louis, et al.; "Enhancing Solubilization in Microemulsions-State of the Art and Current Trends"; Journal of Surfactants and Detergents, vol. 8, No. 1, Jan. 2005, pp. 3-21.

Sheng, J.J.; "Optimum Phase Type and Optimum Salinity Profile in Surfactant Flooding"; Journal of Petroleum Science and Engineering, vol. 75, Nov. 2010, pp. 143-153.

Surtex, Inc.; "Investigation of Oil Recovery Improvement by Coupling an Interfacial Tension Agent and a Mobility Control Agent in Light Oil Reservoirs"; Technical Progress Report, DOE Contract No. DE-AC22-92 BC14886, Sep. 28, 1992, Title and Disclaimer pages, and pp. 1-4.

International Search Report, issued on Feb. 22, 2013, during the prosecution of International Application No. PCT/US2012/055343.

Written Opinion of the International Searching Authority, Feb. 22, 2013, during the prosecution of International Application No. PCT/US2012/055343.

International Search Report, issued on Jun. 2, 2014, during the prosecution of International Application No. PCT/US2014/021077.

Written Opinion of the International Searching Authority, issued on Jun. 2, 2014, during the prosecution of International Application No. PCT/US2014/021077.

International Search Report, issued on Jun. 12, 2014, during the prosecution of International Application No. PCT/US2014/018221.

Written Opinion of the International Searching Authority, issued on Jun. 12, 2014, during the prosecution of International Application No. PCT/US2014/018221.

Arachchilage, Gayani Wasana Premathilake Pinnawala; "Part I: Design and Synthesis of Organic Materials for Dye Sensitized Solar Cells Part II: Qualitative and Semi-Quantitative Study of the Behavior of Surfactant on Crude Oil Recovery Processes"; Thesis, (56) References Cited

OTHER PUBLICATIONS

Aug. 2010, submitted to the Graduate College of Bowling Green State University, pp. i-xiv; and pp. 1-75.
Arpornpong, Noulkamol, et al.; "Ethoxy Carboxylate Extended Surfactant Micellar, Adsorption and Adsolubilization Properties"; Journal of Surfactants and Detergents, 2010, vol. 13, pp. 305-311.
Bhuyan, D., et al.; "Simulation of High-pH Coreflood Experiments Using a Compositional Chemical Flood Simulator"; SPE 21029, Feb. 1991, pp. 307-316.
Fernandez, Alvaro, et al.; "Synthesis of New Extended Surfactants Containing a Carboxylate or Sulfate Polar Group"; Journal of Surfactants and Detergents, vol. 8, No. 2, Apr. 2005, pp. 187-191.
Fife, Bruce; "Coconut Cures Preventing and Treating Common Health Problems with Coconut"; cover page, acknowledgement page, and pp. 184-185.
Forgiarini, Ana M., et al.; "Influence of the Mixed Propoxy/Ethoxy Spacer Arrangement Order and of the Ionic Head Group Nature on the Adsorption and Aggregation of Extended Surfactants"; Journal of Surfactants and Detergents, 2010, vol. 13, pp. 451-458.
Knothe, Gerhard, et al.; "Biodiesel: The Use of the Vegetable Oils and Their Derivatives as Alternative Diesel Fuels"; Chapter 10, pp. 172-208.
Krumrine, P.H., et al.; "Surfactant, Polymer, and Alkali Interactions in Chemical Flooding Processes"; SPE 11778, Jun. 1983, pp. 79-86.
Lachmann, Goetz; "Sasol Olefins & Surfactants ISFOL® $C_{12}$-$C_{32}$ Defined Branched Guerbet Alcohols"; Oct. 2003, pp. 1-12.
Mattil, Karl F., et al.; "Bailey's Industrial Oil and Fat Products", $3^{rd}$ Ed., Interscience Publishers, a Division of John Wiley & Sons, Title and Authors pages, and pp. 176 and 192.
Pope, G.A., et al.; "A Sensitivity Study of Micellar/Polymer Flooding"; Society of Petroleum Engineers of AIME, Dec. 1979, pp. 357-368.

\* cited by examiner

MIXED CARBON LENGTH SYNTHESIS OF PRIMARY GUERBET ALCOHOLS

RELATED APPLICATIONS

The present disclosure is related to, and claims priority from U.S. application Ser. No. 13/233,406, with a filing date of Sep. 15, 2011; U.S. application Ser. No. 13/833,045, with a filing date of Mar. 15, 2013; and U.S. application Ser. No. 13/835,030, with a filing date of Mar. 15, 2013. These disclosures are incorporated herein by reference for all purposes.

TECHNICAL FIELD

The present disclosure generally concerns the field of Guerbet alcohols and the manufacture of additives for use in enhanced oil recovery. In particular cases, the present disclosure concerns a method of manufacturing Guerbet alcohols from a mixture of different carbon length hydrocarbons.

BACKGROUND

Guerbet alcohols are high molecular weight primary alcohols with high-purity beta branching. They have low volatility and lower irritation properties compared to other linear alcohols. The melting point and viscosity of Guerbet alcohols are also reduced compared to other linear alcohols. They exhibit oxidative stability at high temperatures and remain liquid up until hydrocarbon chains lengths of $C_{20}$. Furthermore, Guerbet alcohols are reactive and can be used to make many derivatives, such as nonionic surfactants with a wide range of cloud points, which make them particularly suitable for many different petroleum industry operations. However, the products formed from Guerbet alcohols are predominantly used in the cosmetic industry.

The basic starting point of the Guerbet reaction is a fatty alcohol which undergoes self-condensation through the use of strong basis and/or catalysts such as copper or zinc oxide. The produced Guerbet alcohols are beta-branched primary alcohols with twice the molecular weight of the reactant alcohols minus water. The overall reaction for preparing Guerbet alcohols can be represented by the following equation:

(Equation 1)

wherein subscript indice n is a positive integer greater or equal to 2. For example, if subscript indice n is eleven (11), the reactant alcohol has twelve carbon atoms ($C_{12}$) and the produced Guerbet alcohol has twenty-four carbon atoms ($C_{24}$). Similarly, $C_{16}$ alcohols (n=15) can be combined to make $C_{32}$ Guerbet alcohols. Examples of catalysts that can be used in preparing Guerbet alcohols include nickel, lead salts, oxides of copper, lead, zinc, chromium, molybdenum, tungsten, manganese, palladium compounds, silver compounds, or combinations thereof. Depending on the type of Guerbet alcohol to be produced, dimerization of the reactant alcohol can be carried out at temperatures ranging between about 100° to 300° Celsius.

The table below shows scientific names of $C_6$ to $C_{44}$ Guerbet alcohols and their corresponding chemical formulas.

| Guerbet Alcohol | Guerbet Formula |
|---|---|
| 2-Methyl-1-pentanol | $C_6H_{14}O$ |
| 2-Ethyl-1-hexanol | $C_8H_{18}O$ |
| 2-Propyl-1-heptanol | $C_{10}H_{22}O$ |
| 2-Butyl-1-octanol | $C_{12}H_{26}O$ |
| 2-Pentyl-1-nonanol | $C_{14}H_{30}O$ |
| 2-Hexyl-1-decanol | $C_{16}H_{34}O$ |
| 2-Heptyl-1-undecanol | $C_{18}H_{36}O$ |
| 2-Octyl-1-dodecanol | $C_{20}H_{42}O$ |
| 2-Nonyl-1-tridecanol | $C_{22}H_{46}O$ |
| 2-Decyl-1-tetradecanol | $C_{24}H_{50}O$ |
| 2-Undecyl-1-pentadecanol | $C_{26}H_{54}O$ |
| 2-Dodecyl-1-hexadecanol | $C_{28}H_{58}O$ |
| 2-Tridecyl-1-heptadecanol | $C_{30}H_{62}O$ |
| 2-Tetradecyl-1-octadecanol | $C_{32}H_{66}O$ |
| 2-Pentadecyl-1-nonadecanol | $C_{34}H_{70}O$ |
| 2-Hexadecyl-1-eicosanol | $C_{36}H_{74}O$ |
| 2-Heptadecyl-1-heneicosanol | $C_{38}H_{78}O$ |
| 2-Octodecyl-1-docosanol | $C_{40}H_{82}O$ |
| 2-Nonadecyl-1-tricosanol | $C_{42}H_{86}O$ |
| 2-Eicosyl-1-tetraconsanol | $C_{44}H_{90}O$ |

For most applications, such as for use in the cosmetics industry, Guerbet alcohols are produced in high purity by driving the reaction (e.g., Equation 1) to near completion. Any unreacted monomer alcohol can be "stripped-off" to further enhance the purity of the produced Guerbet alcohol. As a result, highly branched, high molecular weight primary alcohols with near mid-point branching (i.e., large hydrophobes with high-purity beta branching) are produced. Guerbet alcohols tend to be more expensive than other alcohols due to the comprehensive conversion during the alcohol dimerization process and/or the subsequent removal of unreacted monomer alcohol. Accordingly, the cost of producing Guerbet alcohols can be prohibitive, especially for applications needing large quantities of Guerbet alcohols.

Guerbet alcohols are utilized to manufacture the additives, which, for example, can be used as surfactants, wetting agents, emulsifiers, detergents and solubilizers. Surfactants are utilized in various stages of hydrocarbon recovery and processing, such as in drilling operations (e.g., drilling fluids/dispersants), reservoir injection (e.g., fracturing fluids, enhanced oil recovery fluids), well productivity (e.g., acidizing fluids), hydrocarbon transportation, environmental remediation, or a combination thereof. A well-known enhanced oil recovery (EOR) method uses surfactant polymer floods to recover additional oil from reservoirs. The compositions of chemicals used in enhanced oil recovery processes vary depending on the type, environment, and composition of the reservoir formation. Surfactants are commonly used when producing or transporting heavy or extra heavy oils, which generally have an API gravity of less than about 20 degrees API. As used herein, API gravity is the weight per unit volume of oil as measured by the American Petroleum Industries (API) scale. For example, API gravity can be measured according to the test methods provided by the American Society for Testing and Materials (ASTM) in test standard D287-92(2006). Crude oil having an API gravity of less than about 20 degrees API is generally referred to as heavy oil. Crude oil having an API gravity of less than about 10 degrees API is generally referred to as extra heavy oil.

SUMMARY

A general embodiment of the disclosure is a method of synthesizing mixed chain length additives from a mixture of primary alcohols comprising, receiving a mixture of primary alcohols comprising at least two different chain length primary alcohols, reacting the mixture of primary alcohols to produce a mixture of Guerbet alcohols, and producing an additive composition from the mixture of Guerbet alcohols.

In embodiments, the method of producing the additive from the mixture of Guerbet alcohols comprises forming an alkoxylated Guerbet alcohol by reacting a lower weight epoxides with a Guerbet alcohol alkoxylate. In specific embodiments, producing the additive composition from the mixture of Guerbet alcohols comprises forming a Guerbet sulfate by sulfation of the Guerbet alcohol alkoxylate, forming a Guerbet sulfonate by sulfonation of the Guerbet alcohol alkoxylate, or forming a Guerbet carboxylate by carboxylation of a Guerbet alcohol alkoxylate.

Embodiments of the additive composition may also be used in a petroleum industry operation. For example, the additive composition may be used in a petroleum industry operation comprises injecting the additive into a subterranean reservoir in an enhanced oil recovery process. In a specific embodiment, the method comprises determining a molecular weight distribution of additives for use in a specific reservoir, and determining the ratios of primary alcohols needed to produce Guerbet alcohols with the molecular weight distribution, wherein the received mixture of primary alcohols is of the determined primary alcohol ratio.

The mixture of primary alcohols can comprise two primary alcohols, three primary alcohols, four primary alcohols or five primary alcohols. Further, the mixture of primary alcohols can comprise different primary alcohols in equal ratios or in different ratios. In an embodiment, the reaction of the mixture of primary alcohols to produce a mixture of Guerbet alcohols is stopped when a Guerbet alcohol conversion of at least 80% is obtained, and the unreacted primary alcohols can be removed from the mixture of Guerbet alcohols or can be left in the mixture of Guerbet alcohols.

In additional embodiments of the disclosure, the mixture of primary alcohols is derived from a natural source. In some examples, the natural source is palm oil, algal oil, canola oil, castor bean oil, coconut oil, corn oil, cotton oil, fish oil, flaxseed oil, hempseed oil, jatropha oil, lard, mustard seed oil, nut oil, olive oil, palm kernel oil, peanut oil, rapeseed oil, safflower seed oil, soybean oil, sunflower oil, tall oil, tallow, yellow grease, or any oil produced by using the following: bacteria, yeast, fungi, unicellular organisms, and multicellular organisms. In one embodiment, the primary alcohols are derived from a fermentation biosynthesis process.

In additional embodiments of the disclosure, a method for identifying suitable additives for use in enhanced oil recovery includes: obtaining a core sample and a crude oil from an oil-bearing subterranean reservoir; providing a plurality of different Guerbet alcohol-based additives, each selected from the group consisting of a Guerbet alcohol, an alkoxylated Guerbet alcohol, a Guerbet sulfate, a Guerbet sulfonate, a Guerbet carboxylate, and mixtures thereof, wherein the different Guerbet alcohol-based additives have varying carbon numbers in the range from 10 to 60; preparing a plurality of compositions for a phase behavior test, each composition comprising at least one of the different Guerbet alcohol-based additives; conducting a phase behavior test with each of the plurality of compositions to select one or more Guerbet alcohol-based additives that give greater than 90% miscibility with a sample of the crude oil in the phase behavior test; conducting a coreflood analysis, using the core sample from the reservoir, with the selected Guerbet alcohol-based additives; identifying a Guerbet alcohol-based additive that recovers at least 90% of residual oil in the coreflood analysis, wherein the Guerbet alcohol-based additive selected in the coreflood analysis contains a Guerbet alcohol-based additive produced from one or more Guerbet alcohols having a first carbon number modal value.

In some such embodiments, the method further comprises preparing a production Guerbet alcohol-based additive from a Guerbet alcohol mixture having a carbon number modal value equal to the first carbon number modal value; preparing an enhanced oil recovery composition comprising the production Guerbet alcohol-based additive; and injecting the production Guerbet alcohol-based additive into the reservoir for enhanced oil recovery.

In some such embodiments, the Guerbet alcohol mixture is prepared from fatty alcohols produced in a fermentation biosynthesis process.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

Aspects of the present invention describe a method for manufacturing large molecular-weight additives from branched Guerbet alcohols (GAs) derived from a mixture of different carbon length alcohols. In one embodiment, the additives are useful as surfactants in enhanced oil recovery methods. As will be described, the additives and Guerbet alcohols of the present disclosure conform to a specific ratio given the length of the different reacting hydrocarbons and their starting reaction ratios.

Figure 1:
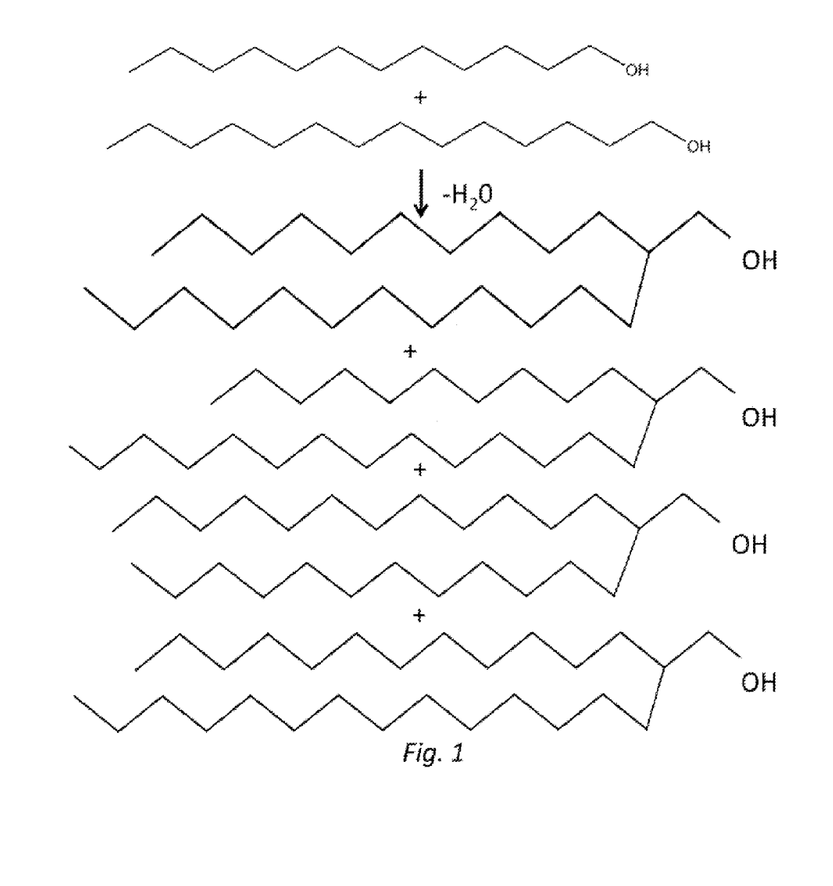
FIG. 1 is an example of a mixed Guerbet reaction illustrating the structures of the starting materials and the products for the reaction of $CH_3(CH_2)_{10}CH_2OH + CH_3(CH_2)_{12}CH_2OH \rightarrow CH_3(CH_2)_{22}CH_2OH + CH_3(CH_2)_{24}CH_2OH + CH_3(CH_2)_{26}CH_2OH$. The reaction with equal moles of alcohol generates the production ration of 1:2:1 $C_{24}OH:C_{26}OH:C_{28}OH$.

In the Guerbet reaction, two alcohols are reacted with or without a catalyst to produce an alcohol which has double the molecular weight of the reactant alcohols, minus a molecule of water generated in the condensation reaction. Commercially available Guerbet alcohols use a single primary alcohol to obtain the double molecular weight structure. However, embodiments disclosed here use a mixture of different carbon length alcohols as the starting material to form a product with a mixture of different length Guerbet alcohols. The reaction of different chain length alcohols, such as $C_{10}$ to $C_{18}$, forms Guerbet alcohol products of molecular weight distributions based on the possible carbon ratio combinations. For example a 1:1 mixture of a $C_{12}$ and $C_{14}$ primary alcohol will produce a 1:2:1 mixture of $C_{24}$, $C_{26}$, and $C_{28}$ Guerbet alcohols, respectively (see FIG. 1). The mixed chain length Guerbet alcohols can be further modified by oxylating the primary alcohol group with ethylene and propylene oxide, etc. These can also be sulfated, sulfonated, carboxylated, etc. in order to produce an additive composition that comprises materials additives with different carbon lengths. Unreacted species may be left in the mixture, further reducing the cost of manufacture.

As used herein, "a" or "an" means "at least one" or "one or more" unless otherwise indicated.

As used herein, the term "essentially equal" or "about," refers to equal values or values within the standard of error of the device that is used to measure the value. The term "substantially equal," as used herein, refers to an amount that is within 3% of the value recited.

As used herein, a "Guerbet alcohol" refers to a primary alcohol with beta branching that has been produced using a Guerbet synthesis reaction.

As used herein, a "Guerbet alcohol-based additive" refers to an additive produced from a Guerbet alcohol. The additive includes at least one Guerbet alcohol in the alcohol, sulfate, sulfonate, alkoxylate or carboxylate form. The Guerbet alcohol-based additive is characterized by a carbon number modal value, which is the carbon number value that is most common in the additive.

As used herein, the term "fatty alcohol" means any saturated or unsaturated, linear or branched alcohol having the structure ROH and comprising at least 8 carbon atoms. The fatty alcohol is not oxyalkylenated or glycerolated. The fatty alcohol may have the structure wherein R is chosen from saturated or unsaturated, linear or branched radicals comprising from 8 to 40, for example, from 8 to 30 carbon atoms. In at least one embodiment, R may be chosen from $C_{12}$-$C_{24}$ alkyl groups and $C_{12}$-$C_{24}$ alkenyl groups. R may optionally be substituted with at least one hydroxyl group. In one embodiment, "fatty alcohol" means a linear saturated alcohol with a terminal —OH and having from 8 to 30 carbon atoms.

As used herein, the term "fatty acid" refers to a hydrocarbon chain having a terminal carboxyl group. In other words, a fatty acid is a carboxylic acid having an aliphatic tail (i.e., a straight or branched non-aromatic hydrocarbon chain). Fatty acids can be described according to the notation (x:y), where x represents the number of carbon atoms in the hydrocarbon chain and y represents the number of double bonds between carbon atoms. For example, $C_{16:2}$ represents 16 carbon atoms and 2 double bonds. Medium-chain fatty acids refer to fatty acids having aliphatic tails of six to twelve carbon atoms and long-chain fatty acids refer to fatty acids having aliphatic tails having greater than twelve carbon atoms. The fatty acids used herein are primarily extracted from the raw material of bio-lipids. Fatty acids often occur as triglycerides, which are three molecules of fatty acids (same or different, e.g., two radicals of oleic acid and one of palmitic acid) joined at the carboxyl groups via ester bonds to hydroxyl groups of glycerol. The fatty acids of the triglyceride can be saturated, monounsaturated, or polyunsaturated.

As used herein, the term "reservoir" refers to an oil-bearing subterranean reservoir from which crude oil may be extracted, unless otherwise noted.

As used herein, a "production" additive or additive composition is intended for injecting into the reservoir for enhanced oil recovery. The term is in contrast to a "test" additive that is tested in a laboratory, pilot plant, or bench scale test protocol to identify suitable additive candidates for the production additive.

Additive properties selected in phase behavior and core-flood test procedures provide the basis for identifying a suitable production additive composition for use in the EOR process. The identified additive composition relates to a mixture of two or more Guerbet alcohol of varying molecular weight, and molecular carbon number.

Selecting a Guerbet alcohol-based additive for use in enhanced oil recovery involves recovering a core sample from the reservoir, and further involves recovering a crude oil sample from the reservoir. Methods for producing core samples, and for recovering crude oil, are readily available and well known.

An EOR composition is prepared for injecting into an oil-bearing subterranean reservoir for enhanced oil recovery (EOR). The composition includes a production Guerbet alcohol-based additive and optionally at least one of a co-surfactant, a co-solvent, brine, and alkali.

The Guerbet alcohol-based additive is a Guerbet alcohol in an alcohol form, or optionally in a sulfate, sulfonate, alkoxylate or carboxylate form. For selecting a Guerbet alcohol-based additive for use in EOR, single Guerbet alcohols or simple mixtures of Guerbet alcohols, containing, for example, from 2-5 different Guerbet alcohols, are prepared for testing. The Guerbet alcohol-based additive in each test sample is differentiated from the others by molecular weight (represented by carbon number) and concentration. A single Guerbet alcohol in a test additive may have a carbon number of 16 to 40 carbon atoms (i.e. 16-40 carbon atoms per Guerbet alcohol molecule). Mixtures of Guerbet alcohols in a test additive may have a range of carbon numbers, generally between 16 and 40. While the test additive may include up to 20 different Guerbet alcohols, each having a different carbon number, the procedure is effective with a simple Guerbet alcohol mixture comprising from 2-10, and in some cases 2-5 Guerbet alcohols of varying molecular weights.

In one embodiment, the Guerbet alcohol-based additive comprises a mixture of Guerbet alcohols of differing carbon numbers, resulting from carbon numbers values of the reactant fatty alcohols from which the mixture is prepared. The Guerbet alcohols used in testing are generally produced from condensation reactions of one or more fatty alcohols; the fatty alcohols may be derived from available sources, including biological sources.

In one embodiment, coconut oil is extracted from the kernels or meat of coconut fruit harvested from coconut trees. Coconut oil is mainly comprised of glycerol esters of medium-chain and long-chain fatty acids, about half (e.g., 45-55%) of which is Lauric acid (saturated $C_{12}$ fatty acid). Coconut oil also typically comprises about eight to about twenty percent each of Myristic acid (saturated $C_{14}$ fatty acid) and Palmitic acid (saturated $C_{16}$ fatty acid), and comprises about five to about ten percent each of Caprylic acid (saturated $C_8$ fatty acid), Capric acid (saturated $C_{10}$ fatty acid), and Oleic acid (monounsaturated $C_{18}$ fatty acid). As will be described later herein, because coconut oil is rich in $C_{12}$ fatty acids, it is a particularly suitable feedstock for $C_{24}$ Guerbet alcohol. Further, currently many of the world's largest producers of coconut oil (e.g., Southeast Asia) are within close proximity to petroleum industry operations where the products of Guerbet alcohols, such as surfactants, can be utilized.

In one embodiment, palm oil is extracted from the pulp of fruit harvested from palm trees. Palm oil is mainly comprised of glycerol esters of long-chain fatty acids, about forty to about fifty percent of which is Palmitic acid (saturated $C_{16}$ fatty acid). Palm oil also typically comprises about thirty to about forty percent of Oleic acid (monounsaturated $C_{18}$ fatty acid), about five to about fifteen percent of Linoleic acid (polyunsaturated $C_{18}$ fatty acid), and about three to six percent of Stearic acid (saturated $C_{18}$ fatty acid). As will be described later herein, because palm oil is rich in $C_{16}$ and $C_{18}$ fatty acids, it is a particularly suitable feedstock for $C_{32}$ and $C_{36}$ Guerbet alcohols. Further, currently many of the world's largest producers of palm oil (e.g., Southeast Asia) are within close proximity to petroleum industry operations where the products of Guerbet alcohols can be utilized.

In one embodiment, palm kernel oil is extracted from the kernels of palm trees. Palm kernel oil is mainly comprised of glycerol esters of medium-chain and long-chain fatty acids, about forty-five to about fifty-five percent of which is Lauric acid (saturated $C_{12}$ fatty acid). Palm kernel oil also typically comprises about fifteen to about twenty percent each of Myristic acid (saturated $C_{14}$ fatty acid) and Oleic acid (monounsaturated $C_{18}$ fatty acid), and comprises about five to about ten percent of Palmitic acid (saturated $C_{16}$ fatty acid). As will be described later herein, because palm kernel oil is rich in $C_{12}$ fatty acids, it is a particularly suitable feedstock for $C_{24}$ Guerbet alcohol. Similar to palm oil, the world's largest producers of palm kernel oil are within close proximity to petroleum industry operations where the products of Guerbet alcohols can be utilized.

In one embodiment, oil is extracted from the castor bean. Castor bean oil is mainly comprised of glycerol esters of long-chain fatty acids, about eight-five percent to about ninety-five percent of which is Ricinoleic acid (monounsaturated $C_{18}$ fatty acid). It also typically comprises about one to six percent each of Oleic acid (monounsaturated $C_{18}$ fatty acid) and Linoleic acid (polyunsaturated $C_{18}$ fatty acid). As will be described later herein, because castor bean oil is rich in $C_{18}$ fatty acids, it is a particularly suitable feedstock for $C_{36}$ Guerbet alcohol. India, Brazil, and China are currently the largest producers of castor bean oil.

In one embodiment, nut oil is utilized. For example, the nut oils can be comprised of glycerol esters of medium-chain and long-chain fatty acids. For example, some nut oils comprise about thirty-five to about sixty percent of Oleic acid (monounsaturated $C_{18}$ fatty acid) and about ten to about forty percent of Linoleic acid (polyunsaturated $C_{18}$ fatty acid). Nut oils can also comprise about five to about fifteen percent of Palmitic acid (saturated $C_{16}$ fatty acid) and about two to six percent of Stearic acid (saturated $C_{18}$ fatty acid). As will be described later herein, because nut oil is rich in $C_{16}$ and $C_{18}$ fatty acids, it is a particularly suitable feedstock for $C_{32}$ and $C_{36}$ Guerbet alcohols.

In one embodiment, a blend of medium-chain and/or long-chain fatty acids is utilized for manufacturing Guerbet alcohols. The blend of fatty acids can be fully or partially extracted from one or more bio-lipids. The blend can include a high percentage of $C_{12}$ through $C_{18}$ fatty acids, such as Lauric acid ($C_{12}$:0), Myristic acid ($C_{14}$:0), Palmitic acid ($C_{16}$:0), Stearic acid ($C_{18}$:0), Palmitoleic acid ($C_{16}$:1), Oleic acid ($C_{18}$:1), Ricinoleic acid ($C_{18}$:1), Vaccenic acid ($C_{18}$:1), Alpha-Linoleic acid ($C_{18}$:2), Gamma-Linolenic acid ($C_{18}$:3), or a combination thereof. For example, the percentage of $C_{12}$ through $C_{18}$ fatty acids in the blend can be greater than about 50 percent. In another example, the percentage of $C_{12}$ through $C_{18}$ fatty acids in the blend is greater than about 80 percent. In another example, the percentage of $C_{12}$ through $C_{18}$ fatty acids in the blend is greater than about 90 percent. In each of these embodiments, while a fatty acid composition might be rich in $C_{12}$ through $C_{18}$ fatty acids, it can also contain fatty acids smaller than $C_{12}$ and greater than $C_{18}$, such as $C_8$ or $C_{20}$ fatty acids, respectively. Medium-chain and long-chain fatty acids are particularly useful for making highly branched, high molecular weight primary alcohols (Guerbet alcohols), which can then be used for making very large hydrophobe surfactants that are used for obtaining ultra-low interfacial tensions and low micro-emulsion viscosities.

Other fatty acid compositions of bio-lipids can be found in the following publications: Swern, D., "Bailey's Industrial Oil and Fat Products," $3^{rd}$ ed., Interscience Publishers, New York, N.Y., 1964, pp. 176 and 192; Ang, Catharina Y. W., KeShun Liu, and Yao-Wen Huang, "Asian Foods: Science and Technology," Technomic Publishing Company, Inc., Lancaster, Pa., 1999; Fife, Bruce, "Coconut Cures," Piccadilly Books, Ltd., Colorado Springs, Colo., 2005, pp. 184 and 185; Knothe, G., Dunn, R. O., Bagby, M. O., "Biodiesel: The Use of Vegetable Oils and Their Derivatives as Alternative Diesel Fuels." Fuels and Chemicals from Biomass. Presented at American Chemical Society Symposium, Ser. 666, Washington D.C., 1997.

There are many processes for breaking down the triglyceride bonds to convert the aforementioned bio-lipids to fatty acid alkyl esters such as transesterification, blending, microemulsions, and pyrolysis. Transesterification is the most common method used for producing fatty acid alkyl esters from bio-lipid. The term "transesterification" (as well as derivatives, other forms of this term, and linguistically related words and phrases), as used herein, generally refers to the process of forming an ester by reacting one or more fatty acids with an alcohol, typically in the presence of a catalyst. More specifically, this term refers to the process of converting bio-lipids to fatty acid alkyl esters and glycerin. Generally, the bio-lipid raw materials, or the fatty acids and triglycerides obtained after subjecting the bio-lipid raw materials to separation, are reacted with a low-molecular weight alcohol in the presence of a catalyst to produce fatty acid alkyl esters and glycerin. In most applications, the low-molecular weight alcohol is methanol or ethanol. Other possible low-molecular weight alcohols include propanol and butanol. Catalysts accelerate the chemical reaction by reducing the activation energy (i.e., the energy needed to initiate the reaction). Examples of catalysts (or biocatalysts) include acids (e.g., hydrochloric acid, sulfuric acid, sulfonic acid, heteropoly acid, a Lewis acid, a Brønsted acid), a Brønsted acidic ionic liquid, organic or inorganic bases, enzymes, lipase, and an alkoxide, a carbonate, or a hydroxide of sodium, potassium, calcium, or barium. Sodium hydroxide (NaOH), potassium hydroxide (KOH), sodium methoxide (NaOCH₃), and potassium methoxide (KOCH₃) are the most common alkali catalysts used for transesterification.

For example, the transesterification of a triglyceride with methanol to produce methyl ester and glycerin is represented by the following equation, where sodium methoxide is used as a used as the base catalyst:

(Equation 2)

In Equation 2, R represents an aliphatic group, such as an alkyl group, comprising typically between about 4 and about 22 carbon atoms. The triglycerides react with the low molecular weight alcohol to convert molecules of fat to fatty acid alkyl esters and glycerin. The fatty acid alkyl esters can be separated from the glycerin during the transesterification reaction or after its completion. For example, separation can be accomplished using a separator, a centrifuge, a filtration mechanism, adsorption, distillation, extraction, suitable reagents, or by allowing the glycerin to naturally settle due to gravity.

Accordingly, transesterification of the bio-lipid results in one or more fatty acid alkyl esters including, but not limited to, algal oil alkyl ester, castor bean oil alkyl ester, canola oil alkyl ester, coconut oil alkyl ester, corn oil alkyl ester, cotton oil alkyl ester, fish oil alkyl ester, flaxseed oil alkyl ester, hempseed oil alkyl ester, jatropha oil alkyl ester, lard alkyl ester, mustard seed oil alkyl ester, nut oil alkyl ester, olive oil alkyl ester, palm oil alkyl ester, palm kernel oil alkyl ester, peanut oil alkyl ester, rapeseed oil alkyl ester, safflower seed oil alkyl ester, soybean oil alkyl ester, sunflower oil alkyl ester, tall oil alkyl ester, tallow alkyl ester, yellow grease alkyl ester, or any alkyl ester produced from an oil of a bacteria (naturally-occurring or genetically engineered), yeast, fungi, unicellular organism, or multicellular organism.

The fatty acid alkyl esters, such as fatty acid methyl ester, are then reduced to fatty alcohols (natural alcohols), which typically are aliphatic alcohols having a chain of 8 to 22 carbon atoms. In one embodiment, the esters of fatty acids are hydrogenated using a catalyst, such as copper chromite. For example, the catalytic hydrogenation of fatty acid methyl ester producing a fatty alcohol and methanol is represented by the following equation:

(Equation 3)

wherein R represents an aliphatic group (either a straight or branched non-aromatic hydrocarbon chain), such as an alkyl group. Functional group R typically comprises between about 4 and about 22 carbon atoms.

In one embodiment, the fatty alcohols are derived from a fermentation biosynthesis process. In another embodiment, the fatty alcohols are derived from triglyceride hydrolysis. In triglyceride hydrolysis, one or more fatty acids are reacted with an alcohol, typically in the presence of a catalyst, to form an ester. In most applications, the alcohol is a low-molecular weight alcohol such as methanol or ethanol. Other possible low-molecular weight alcohols include propanol and butanol. Catalysts accelerate the chemical reaction by reducing the activation energy (i.e., the energy needed to initiate the reaction). Examples of catalysts (or biocatalysts) include acids (e.g., hydrochloric acid, sulfuric acid, sulfonic acid, heteropoly acid, a Lewis acid, a Brønsted acid), a Brønsted acidic ionic liquid, organic or inorganic bases, enzymes, lipase, and an alkoxide, a carbonate, or a hydroxide of sodium, potassium, calcium, or barium. Sodium hydroxide (NaOH), potassium hydroxide (KOH), sodium methoxide (NaOCH₃), and potassium methoxide (KOCH₃) are the most common alkali catalysts used for transesterification. The fatty acid alkyl esters, such as fatty acid methyl ester, are then reduced to fatty alcohols (natural alcohols), which typically are aliphatic alcohols having a chain of 8 to 22 carbon atoms. In one embodiment, the esters of fatty acids are hydrogenated using a catalyst, such as copper chromite.

Each test mixture includes a Guerbet alcohol-based additive and optionally one or more of an alkali, a co-solvent, a co-surfactant, a polymer, and a brine solution. Each of these additional components may be selected on the basis of the reservoir inorganic matrix, including its wettability and surface charge characteristics, and on the composition of the reservoir brine. For purposes of identifying the appropriate balance of Guerbet alcohols in the EOR composition, the concentrations of additional components in the test mixtures may be kept constant, and only the carbon number and concentration of the Guerbet alcohol-based additive varied from test to test.

In the testing protocol, individual test batches comprising a Guerbet alcohol-based additive are compared for phase behavior characteristics. Select batches that are "phase behavior suitable" demonstrate greater than 90% miscibility with a sample of crude oil from the reservoir for which the EOR additive mixture is intended. "Miscibility" refers to the middle layer in a phase behavior test; greater than 90% miscibility refers to the volume of the middle layer as a percentage of the total liquid volume.

At least one test batch that is found to be phase behavior suitable is further tested in a coreflood analysis. Test batches that are further found to be "coreflood suitable" recover at least 90% of residual oil in the coreflood analysis, using a core sample from the reservoir. At least one coreflood suitable additive is selected as the basis for preparing an EOR composition.

The select Guerbet alcohol-based additive is characterized by a single carbon number or a range of carbon numbers, which provide a characteristic carbon number modal value for the additive. The carbon number modal value for each Guerbet alcohol-based additive is the carbon number value that is most common in the additive. For a single Guerbet alcohol-based additive molecule (e.g. a $C_{24}$ Guerbet alcohol) the modal value carbon number is equal to the carbon number (e.g. $C_{24}$). In a Guerbet alcohol-based additive comprising a mixture of Guerbet alcohols (e.g. $C_{24}$:$C_{26}$:$C_{28}$ in a 1:2:1 molar ratio), the carbon number modal value is equal to the most common carbon number in the mixture (e.g. $C_{26}$). In one embodiment, the carbon number modal value of the additive ranges from 10 to 40; in another embodiment from 16 to 40.

The carbon number modal value which is optimized in the testing protocol is the basis for preparing the EOR composition. In one embodiment, the EOR composition includes a Guerbet alcohol-based additive having the same carbon number modal value as that of the select test batch. The Guerbet alcohol-based additive may be of a single Guerbet alcohol-based molecule, or of a mixture of molecules having different carbon numbers. In one embodiment, the Guerbet alcohol-based additive is prepared from mixtures of fatty alcohols which are produced in a fermentation biosynthesis process. Fatty alcohols from the fermentation biosynthesis process may have a range of carbon numbers, such as between 5 and 30, and in one embodiment between 8 and 20. These fatty alcohols are reacted in a Guerbet alcohol reaction to form a mixture of Guerbet alcohols having a carbon number modal value equal to the carbon number modal value of the select test sample from the phase behavior and coreflood analyses.

In one embodiment, the EOR composition comprises a production Guerbet alcohol-based additive that is the same as the Guerbet alcohol-based additive selected using the testing protocol. In one embodiment, the production Guerbet alcohol-based additive differs in the particular type and ratio of Guerbet alcohols, while maintaining a carbon number modal value that is the same as that of the select Guerbet alcohol-based additive from the testing protocol.

Additive compositions are analyzed in a phase behavior test to identify compositions that are suitable for high oil recovery from a reservoir. There are many benefits in using phase behavior as a screening method. Phase Behavior studies are used to determine: (1) the effect of electrolytes; (2) oil solubilization, IFT reduction, (3) microemulsion densities; (4) surfactant and microemulsion viscosities; (5) coalescence times; (6) identify optimal surfactant/cosolvent formulations; and/or (7) identify optimal formulation for coreflood studies. In general, the phase behavior test may be conducted on a combination of crude oil from the reservoir and an aqueous additive composition, which includes the test additive or additive mixture, and may also include one or more of a co-surfactant, a co-solvent, brine, and an alkali.

An exemplary phase behavior test is described and taught in "Identification and Evaluation of High-Performance EOR Surfactants," D. B. Levitt, A. C. Jackson, C. Heinson, L. N. Britton, T. Malik, V. Dwarakanath, and G. A. Pope, *SPE Reservoir Evaluation & Engineering* (SPE 100089-PA-P), April 2009, p. 243-253, the entire disclosure of which is incorporated herein by reference. A phase behavior test may be conducted, as an illustrative example, by the following. Two mL of each prospective surfactant slug formulation are pipetted into a, 5 mL glass pipette with a flame-sealed bottom end. The level of the aqueous surfactant solution is recorded. Two mL of hydrocarbon is added and argon is used to displace volatile gas so that the tops of pipettes could be safely flame sealed. Pipettes are then placed in an oven at reservoir temperature. After reaching the desired test temperature, pipettes are inverted several times to facilitate mixing. Phase volumes are then observed and recorded over time. Phase behavior of surfactant/co-surfactant/co-solvent formulations is evaluated by qualitative visual observation, including how fast the emulsions break after gentle mixing and form a microemulsion in equilibrium with oil and/or brine, solubilization ratio at optimum salinity, formation of microemulsion with low viscosity, and aqueous stability of surfactant/polymer solutions at required injection salinity.

Individual or mixtures of Guerbet alcohol-based additives may be evaluated for phase behavior performance. In one embodiment, each Guerbet alcohol-based additive evaluated in the phase behavior test is prepared from a Guerbet alcohol. Likewise, mixtures of Guerbet alcohol-based additives are prepared from a mixture of Guerbet alcohols having between 10 and 60, and in another embodiment between 16 and 40 carbon atoms per molecule. In one embodiment, the mixture of Guerbet alcohols used in preparing each mixture of Guerbet alcohol-based additives has a number of carbon atoms that differs by at most 2 carbon atoms from at least one other of the Guerbet alcohols used in the preparation.

In one embodiment, the Guerbet alcohol-based additive, generally in aqueous solution, is tested with crude oil in the phase behavior test. In another embodiment, the Guerbet alcohol-based additive is combined with one or more of a co-additive, a co-solvent, brine, and alkali for the test.

Results from the phase behavior studies may be further investigated in coreflood studies with core samples from the oil-bearing subterranean formation. In the coreflood method, a core sample of reservoir rock is flooded with a sequence of liquid treatments, some at reservoir pressure, to evaluate the effect of enhanced oil recovery methods on the reservoir. The liquid treatments may include, for example, flooding with brine, with water, with a polymer composition, with an additive composition, or any combination, in any order. Coreflood methods are well known in the art. For example, various additives may be evaluated in the coreflood method to identify the additive, or the particular additive properties, which are suitable for effective removal of oil from the reservoir.

Coreflood tests are known in the art. In one embodiment, a core sample from the reservoir is oil flooded, and then additive flooded using a test Guerbet alcohol-based additive mixture. The additive mixture is then removed from the core sample, and the core sample evaluated for residual oil. The additive mixtures that are evaluated in the coreflood analysis are selected from the samples which meet or exceed a target solubility measure in the phase behavior test, where the target solubility measure is greater than 70%, and in another embodiment greater than 80%, and in another embodiment greater than 90%, and in another embodiment greater than 95% miscibility of aqueous and oil phases in the phase behavior test.

At least one Guerbet alcohol-based additive mixture that is identified in the coreflood test as recovering at least 90% of residual oil is selected for injecting into the reservoir for enhanced oil recovery.

A Guerbet alcohol-based additive may be a Guerbet alcohol, a chemical compound derived from reacting a Guerbet alcohol, or mixtures thereof. Additives that are derived from reactions with Guerbet alcohols include alkoxylated Guerbet alcohols and Guerbet sulfates. In one embodiment, the Guerbet alcohols are chemically treated to modify, and often to improve, their performance as additives for a particular reservoir or family of reservoirs.

The Guerbet alcohols are prepared by combining fatty alcohols in a condensation reaction that combines two fatty alcohol molecules and generates a molecule of water:

$$C_nH_{2n}OH + C_mH_{2m}OH = C_{n+m}H_{2n+2m}OH + H_2O \quad \text{(Equation 4)}$$

Fatty or natural alcohols can be used to produce Guerbet alcohols through a dimerization process. In one embodiment, a Guerbet alcohol is prepared by the combination of two fatty alcohol molecules in the presence of a base, such as NaOH or KOH. The alcohols and base mixture are stirred and heated to Guerbet reaction temperatures (220-300° C.) with nitrogen purging to remove produced water. The reaction is continued until at least 50% of the fatty alcohols have been converted. In embodiments, the reaction proceeds until at least 70%, or 90% of the fatty alcohols have been converted. The reaction mixture may then be filtered to remove the unreacted base. In one embodiment, the Guerbet alcohol synthesis is conducted in the presence of a metal catalyst, such as a zinc-cobalt or copper-nickel catalyst.

The Guerbet alcohol may be prepared from a fatty alcohol, i.e. an unbranched paraffinic alcohol having in a range from $C_{10}$ to $C_{30}$ carbon atoms and a terminal —OH group providing the alcohol function. Conventional Guerbet reactions use a pure primary alcohol chain, from $C_{10}$ to $C_{18}$, which is then reacted with itself. In one embodiment, the Guerbet alcohol is prepared by a combination of two molecules of a single fatty alcohol having in a range from C10 to C30 carbon atoms. In one embodiment, a mixture of fatty alcohols may be used in the Guerbet preparation to form a mixture of different carbon chain length Guerbet alcohols. For example, the mixture may comprise $C_{10}$ and $C_{12}$ or the mixture could also comprise $C_{14}$ and $C_{18}$.

In an embodiment of the disclosure, mixtures of different carbon length alcohols are used as the primary feedstock for Guerbet alcohols. These feedstock mixtures result in formation of Guerbet alcohol having a distribution of different carbon lengths which, when sulfonated, carboxylated, etc., presents superior enhanced oil recovery properties to the mixture of additive.

The mixture of different length primary alcohols used as feedstock for the Guerbet alcohols may come from a variety of sources. For example, the primary alcohols may be derived from mineral hydrocarbon sources or they may be derived from biologically based sources, providing for a "green" starting material. The "green" starting material could be used without need for excessive cleaning or separation, reducing the environmental foot print and the price of processing the material. The biologically based source may be a bio-lipid, such as a triglyceride. The biologically based sources include palm oil, algal oil, canola oil, castor bean oil, coconut oil, corn oil, cotton oil, fish oil, flaxseed oil, hempseed oil, jatropha oil, lard, mustard seed oil, nut oil, olive oil, palm kernel oil, peanut oil, rapeseed oil, safflower seed oil, soybean oil, sunflower oil, tall oil, tallow, yellow grease, or any oil produced by using the following: bacteria, yeast, fungi, unicellular organisms, and multicellular organisms.

There are many processes for breaking down triglyceride bonds to convert the aforementioned bio-lipids to fatty acid alkyl esters such as transesterification, blending, microemulsions, and pyrolysis. Transesterification is the most common method used for producing fatty acid alkyl esters from bio-lipid. The term "transesterification" (as well as derivatives, other forms of this term, and linguistically related words and phrases), as used herein, generally refers to the process of forming an ester by reacting one or more fatty acids with an alcohol, typically in the presence of a catalyst. More specifically, this term refers to the process of converting bio-lipids to fatty acid alkyl esters and glycerin. Generally, the bio-lipid raw materials, or the fatty acids and triglycerides obtained after subjecting the bio-lipid raw materials to separation, are reacted with a low-molecular weight alcohol in the presence of a catalyst to produce fatty acid alkyl esters and glycerin. In most applications, the low-molecular weight alcohol is methanol or ethanol.

Other possible low-molecular weight alcohols include propanol and butanol. Catalysts accelerate the chemical reaction by reducing the activation energy (i.e., the energy needed to initiate the reaction). Examples of catalysts (or biocatalysts) include acids (e.g., hydrochloric acid, sulfuric acid, sulfonic acid, heteropoly acid, a Lewis acid, a Brønsted acid), a Brønsted acidic ionic liquid, organic or inorganic bases, enzymes, lipase, and an alkoxide, a carbonate, or a hydroxide of sodium, potassium, calcium, or barium. Sodium hydroxide (NaOH), potassium hydroxide (KOH), sodium methoxide ($NaOCH_3$), and potassium methoxide ($KOCH_3$) are the most common alkali catalysts used for transesterification.

The fatty acid alkyl esters, such as fatty acid methyl ester, are then reduced to fatty alcohols (natural alcohols), which typically are aliphatic alcohols having a chain of 8 to 22 carbon atoms. In one embodiment, the esters of fatty acids are hydrogenated using a catalyst, such as copper chromite.

In one embodiment, the fatty alcohols are prepared via a fermentation biosynthesis pathway. Starting from 5-6 carbon chain feedstocks containing sugar, and without the addition of natural oils, these fermentation biosynthesis pathways produce a range of fatty alcohols that are useful for the Guerbet synthesis. Such fermentation biosynthesis pathways are described, for example, in Zheng et al. *Microbial Cell Factories* 2012, 11:65; and U.S. Pat. No. 8,859,259, incorporated herein by reference.

The Guerbet alcohol-based additive mixture contains a mixture of Guerbet alcohol-based molecules, with the Guerbet alcohol-based molecules being prepared from Guerbet alcohols. Each Guerbet alcohol used in preparing the mixture has in a range from 10 to 60 carbon atoms per molecule, in a mole ratio that is reflective of the fatty alcohols from which the mixture is prepared. In one embodiment, each Guerbet alcohol in the mixture has in a range from 16 to 40 carbon atoms per molecule.

A reaction of a binary mixture of fatty alcohols having $C_n$ and $C_m$ molecular carbon numbers respectively produces a mixture of Guerbet alcohols having $C_{2n}$, $C_{n+m}$, and $C_{2m}$ molecular carbon numbers. Reaction of a tertiary mixture of fatty alcohols having $C_n$, $C_m$ and $C_p$ molecular carbon numbers produces a mixture of Guerbet alcohol having $C_{2n}$, $C_{n+m}$, $C_{2m}$, $C_{m+p}$, and $C_{2p}$ molecular carbon numbers, where n, m and p are integer values. In one embodiment, n, m, and p have integer values between 5 and 20.

In some embodiments of the disclosure, the alcohol feedstock mixture consists of two different length primary alcohols, three different length primary alcohols, four different length primary alcohols, five different length primary alcohols, six different length primary alcohols, or seven or more different length primary alcohols. The primary alcohols can be $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, or more than 30 carbon atoms long. The chain lengths may be even, odd, or a combination thereof. The alcohols to be reacted with each other may also include chains of ethylene oxide or propylene oxide. The mixture of primary alcohols may be made from mixing different length primary alcohols together, or the mixture of primary alcohols may occur naturally. The alcohols to be reacted with each other may also include chains of ethylene oxide or propylene oxide.

Ratios of carbon lengths in the prepared Guerbet alcohol mixtures are reflective of the ratios of the fatty alcohol from which they are made. While the range of potential Guerbet alcohol mixtures that can be made from a mixture of fatty alcohols ranging from $C_5$ to $C_{20}$ is large, a few examples illustrate how each Guerbet alcohol mixture can be tailored to match desired additive properties in the Guerbet alcohol-based additive. For example, a mixture of $C_{12}$ and $C_{14}$ fatty alcohols in a 1:1 molar ratio react to form a $C_{24}:C_{26}:C_{28}$ Guerbet alcohol mixture close to a 1:2:1 molar ratio. Likewise, a mixture of $C_{12}$ and $C_{16}$ fatty alcohols in a 4:1 molar ratio react to form a $C_{24}:C_{28}:C_{32}$ Guerbet alcohol mixture close to a 16:8:1 molar ratio. Likewise, a mixture of C10, $C_{12}$, and $C_{14}$ fatty alcohols in a 1:1:1 molar ratio react to form a $C_{20}:C_{22}:C_{24}:C_{26}:C_{28}$ Guerbet alcohol mixture close to a 1:2:3:2:1 molar ratio.

Thus, the composition of the mixture of Guerbet alcohol-based additives that is identified for injecting into the reservoir for enhanced oil recovery directs the selection of a fatty alcohol mixture which is reacted to form the Guerbet alcohol mixture.

In one embodiment of the disclosure, the mixed Guerbet alcohols are utilized to manufacture additives, which, for example, can be used as wetting agents, emulsifiers, detergents and solubilizers. As previously discussed, Guerbet alcohols have many physical properties that make them beneficial for making very large hydrophobe surfactants, which can be used to obtain ultra-low interfacial tensions and low micro-emulsion viscosities. Surfactants are commonly used in the petroleum industry for drilling operations (e.g., drilling fluids/dispersants), reservoir injection (e.g., fracturing fluids, enhanced oil recovery fluids), well productivity (e.g., acidizing fluids), hydrocarbon transportation, environmental remediation, or a combination thereof. The selection of a surfactant for a petroleum industry application typically depends on various factors such as total acid number (TAN), crude-oil composition in the reservoir, and the compatibility with the make-up or injection brine. Standard phase-behavior tests can be conducted to screen for appropriate surfactants.

In some embodiments, Guerbet alcohols are sulfated to obtain Guerbet sulfates. For example, sulfamic acid sulfation can be used. In some embodiments, Guerbet alcohols are sulfonated to obtain Guerbet sulfonates. Alkoxylated Guerbet alcohols can also undergo sulfation or sulfonation to produce large, branched $C_{24}$-$C_{32}$ alkyl alkoxylated additives, such as alkyl sulfate additives or alkyl sulfonates additives. These additives can also be tailored to exhibit desirable phase behaviors for particular reservoir conditions by altering the molecular weight, molecular weight distribution, and branching/point of attachment (e.g., attachment of aryl groups to alkyl groups). The mixed Guerbet alcohols may also be carboxylated to yield a carboxylate additive.

Sulfation of the Guerbet alcohol may be conducted using a chlorosulfonic acid reactant. The Guerbet alcohol to be sulfated is diluted with dichloromethane (150 weight % of Guerbet alcohol) and cooled down to 5-10° C. Chlorosulfonic acid (1.1 eq) is added to maintain the temperature to no higher than 10° C. The reaction mixture is then allowed to warm to room temperature and stirred for 4 hours under constant nitrogen gas flow. This reaction mixture is added dropwise to an aqueous NaOH solution, while the temperature is maintained below 15° C. Sufficient NaOH is supplied to maintain the pH at the end of the addition in a range from 9 to 10. Dichloromethane is removed under vacuum in a rotary evaporator at temperature below 50° C., and the desired sulfated product is recovered.

One example of an additive that can be manufactured from a Guerbet alcohol is an anionic additive. Some anionic additives, such as sulfates, sulfonates, phosphates, and carboxylates are described in the art in, for example, SPE 129907 and U.S. Pat. No. 7,770,641, which are both incorporated herein by reference. Non-ionic additives include alcohol alkoxylates such as alkylaryl alkoxy alcohols or alkyl alkoxy alcohols. In some embodiments, non-ionic additives manufactured form Guerbet alcohols are combined with other non-ionic additives such as non-ionic esters.

In some embodiments the Guerbet alcohols are alkoxylated to form alkoxylated Guerbet alcohols. Here, lower weight epoxides, such as ethylene oxide (EO), propylene oxide (PO), and butylenes oxide (BO), are added to the Guerbet alcohols. In some embodiments, more than six (6) repeating units, such as EO, are present. In some embodiments, more than ten to twenty repeating units, such as EO, are present. In embodiments, there are less than 35 EO and less than 10 PO, or a mixture thereof. These lower weight epoxides are typically used to tailor the additive such that it exhibits a desirable phase behavior for particular reservoir conditions, such as electrolyte concentrations (salinities), temperature, and hydrocarbon compositions. Accordingly, a desired HLB (Hydrophillic-Lipophillic-Balance) can be achieved by tailoring the number of alkoxylates attached to the Guerbet alcohol, as well as tailoring the ratios of the feedstock primary alcohols in the mixture.

Alkoxylation of the Guerbet alcohol may be conducted in the presence of a KOH catalyst. Reaction of the Guerbet alcohol in the presence of the catalyst may be conducted at a temperature of 100° C. and at 20 mbar for 2 hours, during which time water is removed to drive the equilibrium toward the desired products. The mixture is then flushed, the pressure increased to 1.3 bar and the temperature increased while alkylene oxides are added (125° C.-135° C. in case of ethylene oxide; 130-140° C. in case of propylene oxide; 135-145° C. in case of butylene oxide). After 5 hours stirring at 125-145° C., the reactor is flushed with N2 and cooled to 70° C., and the alkoxylated Guerbet alcohol recovered.

In embodiments of the disclosure, the mixed length Guerbet additives disclosed herein provide enhanced phase behavior and solubility profiles for use in additive polymer floods during enhanced oil recovery methods. Once a mixed length additive composition has been optimized for a specific formation, the ratios of the starting alcohols can be back calculated to produce the specific ratios of additive lengths needed. In this way, mixed length additive compositions can be tailor made for specific reservoir conditions.

In an embodiment of the disclosure, the use of mixed length alcohols as the starting point for Guerbet alcohols results in a faster reaction rate than found using a pure alcohol as the starting point. Pure Guerbet reactions have been found to yield 60% product in 24 hours, while Guerbet reactions with mixed length starting alcohols can result in 90% yield in 23 hours (See Example 1).

In one embodiment, additives are utilized for environmental treatment of wastes (ex situ and/or in situ). In particular, at least one additive manufactured using mixed Guerbet alcohols is used to enhance chemical treatment of contaminated soil or sediment. The contaminant may be organic, such as oil or solvent, or inorganic, such as mercury and arsenic. The additive reduces the interfacial tension between oil and water, thereby increasing the solubility of the contaminant.

The Guerbet alcohol-based additive composition includes a mixture of Guerbet alcohol-based additives. One or more other components may be included, such as one or more polymers, co-additives, alkali, chelators, co-solvents, reducing agents/oxygen scavengers, and biocides.

Water soluble polymers, such as those commonly employed for enhanced oil recovery, are included to control the mobility of the injection solution. Such polymers include, but are not limited to, biopolymers such as xanthan gum and scleroglucan and synthetic polymers such as partially hydrolyzed polyacrylamides (HPAMs or PHPAs) and hydrophobically-modified associative polymers (APs). Also included are co-polymers of polyacrylamide (PAM) and one or both of 2-acrylamido 2-methylpropane sulfonic acid (and/or sodium salt) commonly referred to as AMPS (also more generally known as acrylamido tertiobutyl sulfonic acid or ATBS) and N-vinyl pyrrolidone (NVP). Molecular weights (Mw) of the polymers range from about 100,000 Daltons to about 30,000,000 Daltons, such as about 100,000 to about 500,000, or about 1,000,000 to about 20,000,000 Daltons. In specific embodiments of the invention the polymer is about 2,000,000 Daltons, about 8,000,000 Daltons, or about 20,000,000 Daltons. The polymer and the size of the polymer may be tailored to the permeability, temperature and salinity of the reservoir.

When the CEOR composition is injected as a slug into a subterranean reservoir, effective amounts of polymer are concentrations that allow the slug to efficiently sweep the reservoir. The required viscosity is a function of mobility ratio. Mobility ratio (M) is defined as water (or ASP) relative permeability divided by oil relative permeability multiplied by oil viscosity divided by water (or ASP) viscosity (krw/kro*$\mu$o/$\mu$w). Generally a unit mobility ratio, M=1, or lower is desired in an ASP flood. In one example, the effective amount of polymer added to each slug is sufficient to reduce the viscosity of each subsequent slug, in order obtain favorable mobility ratio throughout the entire flood process. For example, effective amounts of polymer include, but are not limited to about 250 ppm to about 5,000 ppm, such as about 500 to about 2500 ppm concentration, or about 750 to 3000 ppm in order to achieve a favorable mobility ratio under the reservoir conditions of temperature. Different slugs may comprise different amounts of polymer.

Co-surfactants may be included to further lower the interfacial tension between the oil and water phase to less than about 0.01 dyne/cm (for example) and thereby recover additional oil by mobilizing and solubilizing oil trapped by capillary forces. Examples of surfactants that can be utilized include, but are not limited to, anionic surfactants, cationic surfactants, amphoteric surfactants, non-ionic surfactants, or a combination thereof. Anionic surfactants can include sulfates, sulfonates, phosphates, or carboxylates. Such anionic surfactants are known and described in the art in, for example, U.S. Pat. No. 7,770,641, incorporated herein by reference in full. Examples of specific anionic surfactants include internal olefin sulfonates, isomerized olefin sulfonates, alkyl aryl sulfonates, medium alcohol (C10 to C17) alkoxy sulfates, alcohol ether [alkoxy]carboxylates, and alcohol ether [alkoxy]sulfates. Example cationic surfactants include primary, secondary, or tertiary amines, or quaternary ammonium cations. Example amphoteric surfactants include cationic surfactants that are linked to a terminal sulfonate or carboxylate group. Example non-ionic surfactants include alcohol alkoxylates such as alkylaryl alkoxy alcohols or alkyl alkoxy alcohols. Other non-ionic surfactants can include alkyl alkoxylated esters and alkyl polyglycosides. In some embodiments, multiple non-ionic surfactants such as non-ionic alcohols or non-ionic esters are combined. As a skilled artisan may appreciate, the surfactant(s) selection may vary depending upon such factors as salinity, temperature, and clay content in the reservoir. The surfactants can be injected in any manner such as continuously or in a batch process.

The alkali employed is a basic salt of an alkali metal from Group IA metals of the Periodic Table. In an embodiment, the alkali metal salt is a base, such as an alkali metal hydroxide, carbonate or bicarbonate, including, but not limited to, sodium carbonate, sodium bicarbonate, sodium hydroxide, potassium hydroxide, sodium silicate, tetrasodium EDTA, sodium metaborate, sodium citrate, and sodium tetraborate. The alkali is typically used in amounts ranging from about 0.3 to about 20 weight percent of the solution, such as about 0.5 to about 5 weight percent. Use of the alkali may serve to maintain additive in a high pH environment, thereby minimizing additive adsorption. Alkali also protects the additive from hardness.

Additional additives that may be used in the additive composition include chelators, co-solvents, reducing agents/oxygen scavengers, and biocides. Chelators may be used to complex with multivalent cations and soften the water in the solution. Examples of chelators include ethylenediaminetetraacetic acid (EDTA) which can also be used as an alkali, methylglycinediacetic acid (MGDA). Chelants may be utilized to handle hard brines. The amount of chelant may be selected based on the amount of divalent ions in the slug solutions. For example, chelating agents can be used a 10:1 molar ratio with divalent cations such as calcium or magnesium. Other chelating agents may work depending on the brine composition and the desired pH.

Co-solvents may also be included in the slug compositions. Suitable co-solvents are alcohols, such as lower carbon chain alcohols like isopropyl alcohol, ethanol, n-propyl alcohol, n-butyl alcohol, sec-butyl alcohol, n-amyl alcohol, sec-amyl alcohol, n-hexyl alcohol, sec-hexyl alcohol and the like; alcohol ethers, polyalkylene alcohol ethers, polyalkylene glycols, poly(oxyalkylene)glycols, poly(oxyalkylene) glycols ethers or any other common organic co-solvent or combinations of any two or more co-solvents. An illustrative co-solvent, glycol butyl ether (EGBE), is typically used at from 0.75 to 1.5 times the concentration of the additive in the additive composition. Generally, the co-solvent when used may be present in an amount of about 0.5 to about 6.0 weight percent of the composition, such as from about 0.5 to about 4.0 weight percent, or about 0.5 to about 3 weight percent.

Reducing agents/oxygen scavengers such as sodium dithionite may be used to remove any oxygen in the mixture and reduce any free iron into Fe2+. They are used to protect synthetic polymers from reactions that cleave the polymer molecule and lower or remove viscosifying abilities. A reduced environment also lowers additive adsorption.

Biocides are used to prevent organic (algal) growth in facilities, stop sulfate reducing bacteria (SRB) growth which "sour" the reservoir by producing dangerous and deadly H2S, and are also used to protect biopolymers from biological life which feed on their sugar-like structures and therefore remove mobility control. Biocides include aldehydes and quaternary ammonium compounds.

Figure 2:
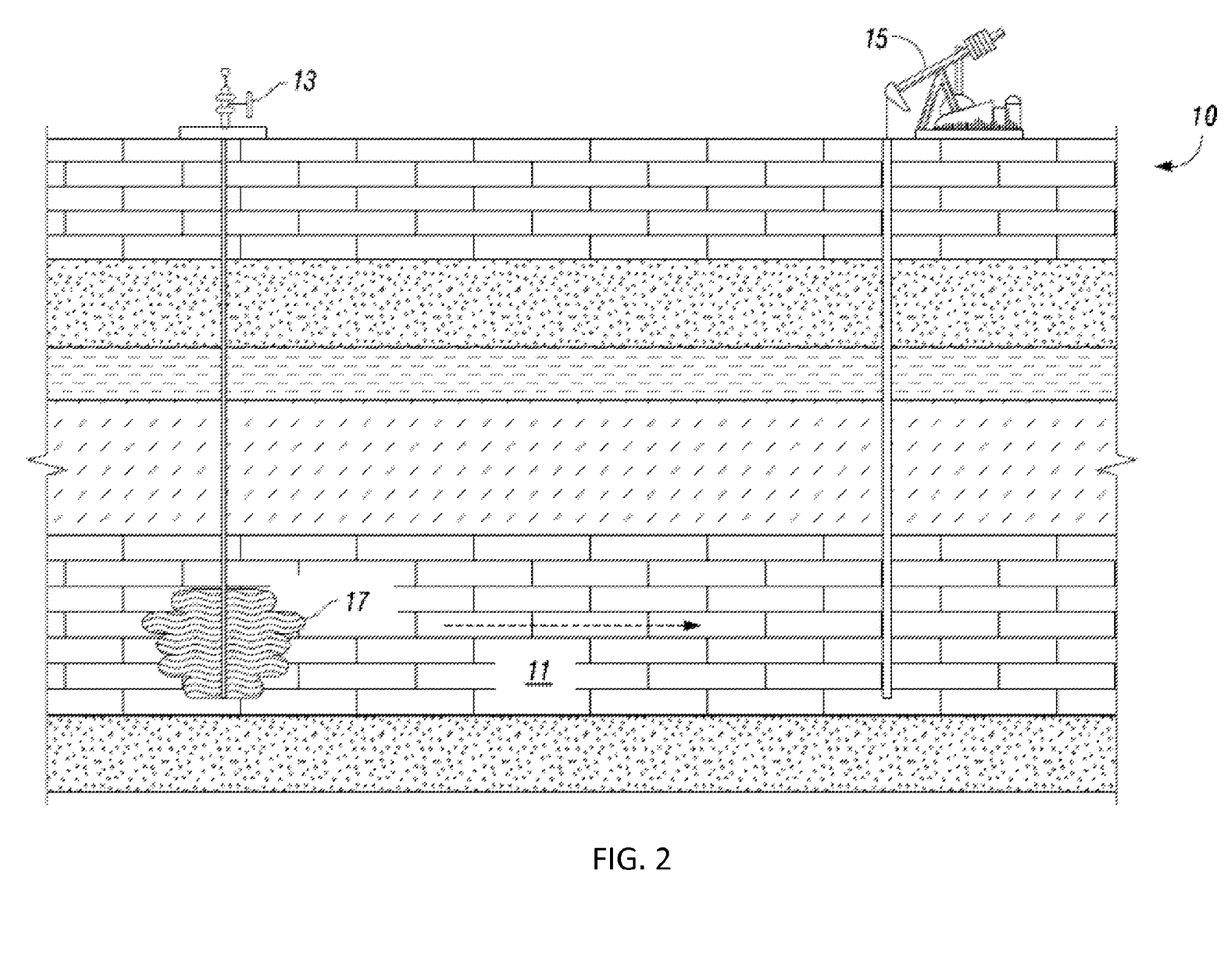
FIG. 2 is a schematic sectional view of a subterranean reservoir that is in fluid communication with an injection well and a production well, according to embodiments of the present invention.

Referring to FIG. 2, a cross-section of subterranean reservoir 10 is shown. Subterranean reservoir 10 includes a plurality of rock layers including hydrocarbon bearing strata or zone 11. Subterranean reservoir 10 can be any type of subsurface formation in which hydrocarbons are stored, such as limestone, dolomite, oil shale, sandstone, or a combination thereof. Injection well 13 extends into hydrocarbon bearing zone 11 of subterranean reservoir 10 such that injection well 13 is in fluid communication with hydrocarbon bearing zone 11. Production well 15 is also in fluid communication with hydrocarbon bearing zone 11 of subterranean reservoir 10 in order to receive hydrocarbons therefrom. Production well 15 is positioned a predetermined lateral distance away from injection well 13. For example, production well 15 can be positioned between 100 feet to 10,000 feet away from injection well 13. As will be readily appreciated by those skilled in the art, additional injection wells 13 and production wells 15 can extend into subterranean reservoir 10 such that multiple production wells 15 optimally receive hydrocarbons being pushed through hydrocarbon bearing zone 11 due to injections from multiple injection wells 13. Furthermore, while not shown in FIG. 2, injection well 13 and production well 15 can deviate from the vertical position such that in some embodiments, injection well 13 and/or production well 15 can be a directional well, horizontal well, or a multilateral well.

In one embodiment, a solution 17 is injected into hydrocarbon bearing zone 11 of subterranean reservoir 10 through injection well 13. Solution 17 comprises an additive composition, such as a surfactant, manufactured from Guerbet alcohols synthesized from one or more fatty alcohols synthesized from a fermentation biosynthesis process. In one embodiment, the Guerbet alcohols are synthesized from one or more hydrocarbon-independent sources of fat (i.e., natural fats or bio-lipids). As previously described, Guerbet alcohols can be synthesized from a bio-lipid by extracting the blend of fatty acids (e.g., Lauric acid, Myristic acid, Palmitic acid, Stearic acid, Palmitoleic acid, Oleic acid, Ricinoleic acid, Vaccenic acid, Linoleic acid, Alpha-Linoleic acid, and Gamma-Linolenic acid) contained therein. Fatty acid alkyl esters are then produced by reacting the blend of fatty acids with a low-molecular weight alcohol. The fatty acid alkyl esters are reduced to a fatty alcohol, which is then dimerized to form the Guerbet alcohol. If solution 17 is a surfactant, the Guerbet alcohol can be reacted with lower weight epoxides to form an alkoxylated Guerbet alcohol, which can further be sulfated or sulfonated. Such surfactants can penetrate into pore spaces of the reservoir formation's rock matrix contacting trapped oil globules, thereby reducing the interfacial tension between the water and oil in the reservoir and releasing the oil from the pore spaces. Surfactants can be injected in any manner such as in an aqueous solution, a surfactant-polymer (SP) flood or an alkaline-surfactant-polymer (ASP) flood. The surfactants can be injected continuously or in a batch process.

In one embodiment, surfactants are utilized for environmental treatment of wastes (ex situ and/or in situ). In particular, at least one surfactant manufactured using Guerbet alcohols synthesized from one or more hydrocarbon-independent sources of fat is used to enhance chemical treatment of contaminated soil or sediment. The contaminant may be organic, such as oil or solvent, or inorganic, such as mercury and arsenic. The surfactant reduces the interfacial tension between oil and water, thereby increasing the solubility of the contaminant.

EXAMPLES

The following examples are included to demonstrate specific embodiments of the disclosure. It should be appreciated by those of skill in the art that the techniques disclosed in the examples that follow represent techniques discovered by the inventors to function well in the practice of the invention, and thus, can be considered to constitute modes for its practice. However, those of skill in the art should, in light of the present disclosure, appreciate that many changes can be made in the specific embodiments disclosed and still obtain a like or similar result without departing from the spirit and scope of the invention.

Example 1

Guerbet Reaction of Mixed Primary Alcohols

This Example covers seven different reactions, each using a different starting mixture of primary alcohols. Table 1 contains the overview of reactants, products and reaction parameters used for the seven different reactions numbered 1-7. Each reaction used 500 grams of the starting reactant mixture at the specified reactant ratio, which was loaded into a reactor with about 0.5 grams of Cu/Ni 80/20 metal powder and 8-9 grams potassium hydroxide (KOH). The reactor was then purged with $N_2$ and heated to the amount specified in the table. The reaction proceeded at 1 atm. Samples were pulled every hour to determine the yield. The yield was calculated by measuring the loss of reactants (starting material) with GC gas chromatography. The starting materials in reactions 6 and 7 were prepared from biologically derived alcohols. The starting material in reaction 6 was derived from a bacterially produced fatty acid, while the starting material for reaction 7 was derived from palm oil.

TABLE 1

| No. | Starting Mixture | Reactant Ratio | Products Found | Product Ratio | % Yield | Rxn Time (Hrs.) | Temp. ° C. |
|---|---|---|---|---|---|---|---|
| 1 | $C_{12}H_{26O}$, $C_{14}H_{28O}$ | 1:1 | $C_{24}$, $C_{26}$, $C_{28}$ | 1:2:1 | 85 | 32 | 236 |
| 2 | $C_{12}H_{26O}$, $C_{14}H_{28O}$ | 1:1 | $C_{24}$, $C_{26}$, $C_{28}$ | 1:2:1 | 90 | 59 | 240 |
| 3 | $C_{10}H_{22O}$, $C_{12}H_{26O}$, $C_{14}H_{28O}$ | 1:1:1 | $C_{20}$, $C_{22}$, $C_{24}$, $C_{26}$, $C_{28}$ | 1:2:4:3:1 | 90 | 23 | 239 |
| 4 | $C_{10}H_{22O}$, $C_{12}H_{26O}$, $C_{14}H_{28O}$, $C_{16}H_{34O}$ | 1:1:1:1 | $C_{20}$, $C_{22}$, $C_{24}$, $C_{26}$, $C_{28}$, $C_{30}$, $C_{32}$ | 1:3:5:7:5:2:1 | 84 | 31 | 250 |
| 5 | $C_{10}H_{22O}$, $C_{12}H_{26O}$, $C_{14}H_{28O}$ | 1:1:1 | $C_{20}$, $C_{22}$, $C_{24}$, $C_{26}$, $C_{28}$ | 1:4:4:3:1 | 58 | 18 | 228 |
| 6 | $C_{12}H_{26O}$, $C_{14}H_{28O}$ | 3.8:1 | $C_{24}$, $C_{26}$, $C_{28}$ | 16:8:1 | 88 | 27 | 242 |
| 7 | $C_{12}H_{26O}$, $C_{14}H_{28O}$ | 3:1 | $C_{24}$, $C_{26}$, $C_{28}$ | 8:5:1 | 80 | 40 | 237 |

The present application also includes the subject matter of the following:

1A. A method of synthesizing mixed chain length surfactants from a mixture of primary alcohols comprising: receiving a mixture of primary alcohols comprising at least two different chain length primary alcohols; reacting the mixture of primary alcohols to produce a mixture of Guerbet alcohols; and producing a surfactant composition from the mixture of Guerbet alcohols.

2A. The method of claim 1A, where producing the surfactant from the mixture of Guerbet alcohols comprises forming an alkoxylated Guerbet alcohol by reacting a lower weight epoxides with a Guerbet alcohol alkoxylate.

3A. The method of claim 1A, wherein producing the surfactant composition from the mixture of Guerbet alcohols comprises forming a Guerbet sulfate by sulfation of a Guerbet alcohol alkoxylate.

4A. The method of claim 1A, wherein producing the surfactant composition from the mixture of Guerbet alcohol comprises forming a Guerbet sulfonate by sulfonation of the Guerbet alcohol alkoxylate.

5A. The method of claim 1A, further comprising utilizing the surfactant composition in a petroleum industry operation.

6A. The method of claim 5A, wherein utilizing the surfactant composition in a petroleum industry operation comprises injecting the surfactant into a subterranean reservoir in an enhanced oil recovery process.

7A. The method of claim 1A, wherein the mixture of primary alcohols comprises two primary alcohols, three primary alcohols, four primary alcohols or five primary alcohols.

8A. The method of claim 1A, wherein the mixture of primary alcohols comprises different primary alcohols in equal ratios.

9A. The method of claim 1A, wherein the mixture of primary alcohols comprises different primary alcohols in different ratios.

10A. The method of claim 1A, further comprising determining a molecular weight distribution of surfactants for use in a specific reservoir, and determining the ratios of primary alcohols needed to produce Guerbet alcohols with the molecular weight distribution, wherein the received mixture of primary alcohols is of the determined primary alcohol ratio.

11A. The method of claim 1A, wherein reacting the mixture of primary alcohols to produce a mixture of Guerbet alcohols is stopped when a Guerbet alcohol conversion of at least 80% is obtained.

12A. The method of claim 11A, wherein unreacted primary alcohols are removed from the mixture of Guerbet alcohols.

13A. The method of claim 1A, wherein the mixture of primary alcohols is derived from a natural source.

14A. The method of claim 13A, wherein the natural source is palm oil, algal oil, canola oil, castor bean oil, coconut oil, corn oil, cotton oil, fish oil, flaxseed oil, hempseed oil, jatropha oil, lard, mustard seed oil, nut oil, olive oil, palm kernel oil, peanut oil, rapeseed oil, safflower seed oil, soybean oil, sunflower oil, tall oil, tallow, yellow grease, or any oil produced by using the following: bacteria, yeast, fungi, unicellular organisms, and multicellular organisms.

15A. The method of claim 1A, wherein producing the surfactant composition from the mixture of Guerbet alcohols comprises forming a Guerbet carboxylate by carboxylation of a Guerbet alcohol.

1B. A method for manufacturing surfactants that are utilized in petroleum industry operations, the method comprising: providing a bio-lipid; reacting the bio-lipid with a low-molecular weight alcohol to produce fatty acid alkyl esters; reducing the fatty acid alkyl esters to a fatty alcohol; dimerizing the fatty alcohol to form a Guerbet alcohol; producing a surfactant from the Guerbet alcohol; and utilizing the surfactant in a petroleum industry operation.

2B. The method of claim 1B, wherein the bio-lipid has a fatty acid composition including at least one medium-chain fatty acid.

3B. The method of claim 1B, wherein the bio-lipid has a fatty acid composition including at least one long-chain fatty acid.

4B. The method of claim 1B, wherein the bio-lipid has a fatty acid composition including one or more fatty acids having aliphatic tails of at least twelve carbon atoms.

5B. The method of claim 1B, wherein the bio-lipid has a fatty acid composition including one or more fatty acids having aliphatic tails of at least sixteen carbon atoms.

6B. The method of claim 1B, wherein the bio-lipid has a fatty acid composition of which at least fifty percent comprises Lauric acid, Myristic acid, Palmitic acid, Stearic acid, Palmitoleic acid, Oleic acid, Ricinoleic acid, Vaccenic acid, Linoleic acid, Alpha-Linoleic acid, Gamma-Linolenic acid, or a combination thereof.

7B. The method of claim 1B, wherein the fatty acid alkyl esters are produced by reacting triglycerides extracted from the bio-lipid with the low-molecular weight alcohol.

8B. The method of claim 1B, wherein the fatty acid alkyl esters are reduced to the fatty alcohol using a catalytic hydrogenation process.

9B. The method of claim 1B, wherein the fatty alcohol includes aliphatic alcohols having between twelve and eighteen carbon atoms.

10B. The method of claim 1B, wherein the Guerbet alcohol includes beta-branched primary alcohols having between twenty-four and thirty-six carbon atoms.

11B. The method of claim 1B, wherein the producing the surfactant from the Guerbet alcohol comprises forming an alkoxylated Guerbet alcohol by reacting lower weight epoxides with the Guerbet alcohol.

12B. The method of claim 1B, wherein the step of producing the surfactant from the Guerbet alcohol comprises forming a Guerbet sulfate by sulfation of the Guerbet alcohol.

13B. The method of claim 1B, wherein the step of producing the surfactant from the Guerbet alcohol comprises forming a Guerbet sulfonate by sulfonation of the Guerbet alcohol.

14B. The method of claim 1B, wherein utilizing the surfactant in a petroleum industry operation comprises injecting the surfactant into a subterranean reservoir in an enhanced oil recovery process.

15B. A method for manufacturing surfactants that are utilized in petroleum industry operations, the method comprising: providing a blend of fatty acids including fatty acids extracted from a bio-lipid, the fatty acids extracted from the bio-lipid including at least one fatty acid selected from the group consisting of Lauric acid, Myristic acid, Palmitic acid, Stearic acid, Palmitoleic acid, Oleic acid, Ricinoleic acid, Vaccenic acid, Linoleic acid, Alpha-Linoleic acid, and Gamma-Linolenic acid; reacting the blend of fatty acids with a low-molecular weight alcohol to produce fatty acid alkyl esters; reducing the fatty acid alkyl esters to a fatty alcohol; dimerizing the fatty alcohol to form a Guerbet alcohol; producing a surfactant from the Guerbet alcohol; and utilizing the surfactant in a petroleum industry operation.

16B. The method of claim 15B, wherein the fatty acids extracted from the bio-lipid comprise triglycerides.

17B. The method of claim 15B, wherein the producing the surfactant from the Guerbet alcohol comprises: reacting the Guerbet alcohol with lower weight epoxides to form an alkoxylated Guerbet alcohol; and sulfating the alkoxylated Guerbet alcohol.

18B. A method for enhancing hydrocarbon recovery in subterranean reservoirs, the method comprising: providing an injection well and a production well that extend into a hydrocarbon bearing zone of a subterranean reservoir and are in fluid communication therewith; forming a solution for injection into the hydrocarbon bearing zone from a Guerbet alcohol that is synthesized from a bio-lipid; injecting the solution into the hydrocarbon bearing zone of the reservoir; and recovering hydrocarbons from the hydrocarbon bearing zone of the subterranean reservoir through the production well.

19B. The method of claim 18B, wherein the Guerbet alcohol is synthesized from the bio-lipid by: extracting fatty acids from the bio-lipid, the fatty acids extracted from the bio-lipid including at least one fatty acid selected from the group consisting of Lauric acid, Myristic acid, Palmitic acid, Stearic acid, Palmitoleic acid, Oleic acid, Ricinoleic acid, Vaccenic acid, Linoleic acid, Alpha-Linoleic acid, and Gamma-Linolenic acid; reacting the blend of fatty acids with a low-molecular weight alcohol to produce fatty acid alkyl esters; reducing the fatty acid alkyl esters to a fatty alcohol; and dimerizing the fatty alcohol to form the Guerbet alcohol.

20B. The method of claim 18B, wherein the forming the solution for injection into the hydrocarbon bearing zone from the Guerbet alcohol that is synthesized from a bio-lipid further comprises: reacting the Guerbet alcohol with lower weight epoxides to form an alkoxylated Guerbet alcohol; and sulfating the alkoxylated Guerbet alcohol.

Although the present invention and its advantages have been described in detail, it should be understood that various changes, substitutions and alterations can be made herein without departing from the spirit and scope of the invention as defined by the appended claims. Moreover, the scope of the present disclosure is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for identifying suitable additives for use in enhanced oil recovery, comprising:
    obtaining a core sample and a crude oil from an oil-bearing subterranean reservoir;
    providing a plurality of different Guerbet alcohol-based additives, each selected from the group consisting of a Guerbet alcohol, an alkoxylated Guerbet alcohol, a Guerbet sulfate, a Guerbet sulfonate, a Guerbet carboxylate and mixtures thereof, wherein the different Guerbet alcohol-based additives have varying carbon numbers in the range from 10 to 60, each Guerbet alcohol-based additive comprising a mixed chain length surfactant synthesized by reacting in a single reactor a mixture of primary alcohols comprising greater than two different chain length primary alcohols in equal parts of each primary alcohol to produce a mixture of Guerbet alcohols, wherein:
        i. the reacting of the mixture of primary alcohols is stopped when a Guerbet alcohol conversion of at least 80% is obtained;
        ii. the number of Guerbet alcohols produced in the mixture of Guerbet alcohols is at least five and is equal to twice the number of primary alcohols in the mixture of primary alcohols minus one; wherein the mixture of Guerbet alcohols comprises:
            a. a lowest molecular weight Guerbet alcohol;
            b. a highest molecular weight Guerbet alcohol; and
            c. a Guerbet alcohol having a molecular weight halfway between the molecular weight of the lowest molecular weight Guerbet alcohol and the highest molecular weight Guerbet alcohol;
        wherein:
            the Guerbet alcohol having the molecular weight halfway between the molecular weight of the lowest molecular weight Guerbet alcohol and the highest molecular weight Guerbet alcohol has a highest concentration of the Guerbet alcohols in the mixture of the Guerbet alcohols;
            the lowest molecular weight Guerbet alcohol and the highest molecular weight Guerbet alcohol each have a lowest concentration of the Guerbet alcohols in the mixture of Guerbet alcohols; and
            remaining Guerbet alcohols in the mixture of Guerbet alcohols have concentrations increasing as molecular weight approaches the molecular weight halfway between the molecular weight of the lowest molecular weight Guerbet alcohol and the highest molecular weight Guerbet alcohol and decreasing as molecular weight approaches the lowest molecular weight Guerbet alcohol and the highest molecular weight Guerbet alcohol; and
        iii. unreacted primary alcohols are removed from the mixture of Guerbet alcohols;
    preparing a plurality of compositions for a phase behavior test, each composition comprising at least one of the different Guerbet alcohol-based additives;
    conducting a phase behavior test with each of the plurality of compositions to select one or more Guerbet alcohol-based additives that give greater than 90% miscibility with a sample of the crude oil in the phase behavior test;
    conducting a coreflood analysis, using the core sample from the reservoir, with the selected Guerbet alcohol-based additives; and
    identifying a Guerbet alcohol-based additive that recovers at least 90% of residual oil in the coreflood analysis, wherein the identified Guerbet alcohol-based additive is used to prepare a production Guerbet alcohol-based composition for enhanced oil recovery.

2. The method of claim 1, further comprising injecting the production Guerbet alcohol-based composition into the oil-bearing subterranean reservoir for enhanced oil recovery.

3. The method of claim 1, wherein the production Guerbet alcohol-based composition comprises a Guerbet alcohol-based additive selected from the group consisting of a Guerbet alcohol, an alkoxylated Guerbet alcohol, a Guerbet sulfate, a Guerbet carboxylate and mixtures thereof.

4. The method of claim 3, wherein the Guerbet alcohol-based additive is prepared from Guerbet alcohols having between 16 and 40 carbon atoms per molecule.

5. The method of claim 1, wherein the production Guerbet alcohol-based composition comprises 0.01-20% by weight of the identified Guerbet alcohol-based additive.

6. The method of claim 1, wherein the production Guerbet alcohol-based composition comprises the identified Guerbet alcohol-based additive and at least one of a co-surfactant, a co-solvent, brine, and alkali.

7. The method of claim 1, wherein the production Guerbet alcohol-based composition comprises 0.3 to 20 weight percent of a basic salt of a Group IA alkali metal.

8. The method of claim 1, wherein the production Guerbet alcohol-based composition comprises 0.3 to 20 weight percent of alkali selected from sodium carbonate, sodium bicarbonate, sodium hydroxide, potassium hydroxide, sodium silicate, tetrasodium EDTA, sodium metaborate, sodium citrate, and sodium tetraborate.

9. The method of claim 1, wherein the production Guerbet alcohol-based composition comprises from 250 ppm to 5,000 ppm of a polymer selected from the group consisting of xanthan gum, scleroglucan, partially hydrolyzed polyacrylamides, hydrophobically-modified associative polymers, co-polymers of polyacrylamide and one or both of 2-acrylamido 2-methylpropane sulfonic acid, and N-vinyl pyrrolidone.

10. The method of claim 1, wherein the production Guerbet alcohol-based composition comprises 0.5 to about 6.0 weight percent of a lower carbon chain alcohol co-solvent.

11. The method of claim 1, further comprising preparing a plurality of compositions for the phase behavior test, each composition comprising at least one of the different Guerbet alcohol-based additives and at least one of a co-surfactant, a co-solvent, brine, and alkali.

12. The method of claim 1, wherein the step of conducting the coreflood analysis further comprises using the core sample from the oil-bearing subterranean reservoir and at least one coreflood suitable additive mixture comprising at least one of the selected Guerbet alcohol-based additives and at least one of a co-surfactant, a co-solvent, brine, and alkali.

* * * * *